US00PP30947P2

(12) United States Plant Patent
Gaydos

(10) Patent No.: US PP30,947 P2
(45) Date of Patent: Oct. 15, 2019

(54) ***PETUNIA* PLANT NAMED 'KL1117MUT1'**

(50) Latin Name: ***Petunia* X *hybrida***
Varietal Denomination: KL1117mut1

(71) Applicant: John P. Gaydos, Rochester, MI (US)

(72) Inventor: John P. Gaydos, Rochester, MI (US)

(73) Assignee: Mary Maxine Johnson, Pugwash, Nova Scotia (CA)

( * ) Notice: Subject to any disclaimer, the term of this patent is extended or adjusted under 35 U.S.C. 154(b) by 0 days.

(21) Appl. No.: 15/998,146

(22) Filed: Jul. 10, 2018

(51) Int. Cl.
*A01H 5/02* (2018.01)

(52) U.S. Cl.
USPC ..... Plt./356.2

(58) Field of Classification Search
USPC ..... Plt./356.2
CPC ... A01H 5/02; A01H 5/00; A01H 6/82; A01H 6/824
See application file for complete search history.

*Primary Examiner* — June Hwu
(74) *Attorney, Agent, or Firm* — C. A. Whealy

(57) ABSTRACT

A new and distinct cultivar of *Petunia* plant named 'KL1117mut1', characterized by its outwardly spreading, mounding to trailing plant habit; freely branching and moderately vigorous growth habit; early and freely flowering habit; single flowers that are violet in color; and good garden performance.

1 Drawing Sheet

Botanical designation: *Petunia* X *hybrida.*
Cultivar denomination: 'KL1117mut1'.

BACKGROUND OF THE INVENTION

The present invention relates to a new and distinct cultivar of *Petunia* plant, botanically known as *Petunia* X *hybrida* and hereinafter referred to by the name 'KL1117mut1'.

The new *Petunia* plant is a naturally-occurring whole plant mutation of *Petunia* X *hybrida* 'KL 1117', disclosed in U.S. Plant Pat. No. 25,485. The new *Petunia* was discovered and selected by the Inventor as a single flowering plant from within a population of plants of 'KL 1117' in a controlled greenhouse environment in Alajuela, Costa Rica on Sep. 10, 2015. Asexual reproduction of the new *Petunia* plant by vegetative tip cuttings in a controlled greenhouse environment in Alajuela, Costa Rica since Sep. 10, 2015, has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'KL1117mut1'. These characteristics in combination distinguish 'KL1117mut1' as a new and distinct *Petunia* plant:

1. Outwardly spreading, mounding to trailing plant habit.
2. Freely branching and moderately vigorous growth habit.
3. Early and freely flowering habit.
4. Single flowers that are violet in color.
5. Good garden performance.

Plants of the new *Petunia* differ primarily from plants of the mutation parent, 'KL 1117', in flower color as plants of 'KL 1117' have white-colored flowers. In addition, leaves of plants of the new *Petunia* are darker green in color than leaves of plants of 'KL1117'.

Plants of the new *Petunia* can be compared to plants of 'Sunsurf Skytatsu', disclosed in U.S. Plant Pat. No. 25,163. In side-by-side comparisons, plants of the new *Petunia* differ primarily from plants of 'Sunsurf Skytatsu' in the following characteristics:

1. Plants of the new *Petunia* are more uniform than plants of 'Sunsurf Skytatsu'.
2. Leaves of plants of the new *Petunia* are darker green in color than leaves of plants of 'Sunsurf Skytatsu'.
3. Plants of the new *Petunia* are more freely flowering than plants of 'Sunsurf Skytatsu'.
4. Flowers of plants of the new *Petunia* are flatter than flowers of plants of 'Sunsurf Skytatsu'.

Plants of the new *Petunia* can also be compared to plants of 'KEllavbu', disclosed in U.S. Plant Pat. No. 13,542. In side-by-side comparisons, plants of the new *Petunia* differ primarily from plants of 'KEllavbu' in the following characteristics:

1. Plants of the new *Petunia* are more freely flowering than plants of 'KEllavbu'.
2. Flowers of plants of the new *Petunia* are flatter than flowers of plants of 'KEllavbu'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet comprises a side perspective view of a typical plant of 'KL1117mut1' grown in a container.

The photograph at the top of the sheet is a close-up view of a typical flowering plant of 'KL1117mut1'.

DETAILED BOTANICAL DESCRIPTION

The aforementioned photographs and following observations and measurements describe plants grown during the spring in 10-cm containers in an acrylic-covered greenhouse in Carleton, Mich. and under cultural practices typical of commercial *Petunia* production. During the production of the plants, day and night temperatures ranged from 18° C. to 24° C. Plants were twelve weeks old when the photographs and description were taken. In the following description, color references are made to The Royal Horticultural Society Colour Chart, 2007 Edition, except where general terms of ordinary dictionary significance are used.

Botanical classification: *Petunia* X *hybrida* 'KL1117mut1'.

Parentage: Naturally-occurring whole plant mutation of *Petunia* X *hybrida* 'KL 1117', disclosed in U.S. Plant Pat. No. 25,485.

Propagation:

*Type*.—Terminal vegetative cuttings.

*Time to initiate roots, summer*.—About three to four days at ambient temperatures ranging from 24° C. to 27° C.

*Time to initiate roots, winter*.—About five to seven days at ambient temperatures ranging from 18° C. to 24° C.

*Time to produce a rooted young plant, summer*.—About three weeks at ambient temperatures ranging from 24° C. to 27° C.

*Time to produce a rooted young plant, winter*.—About four weeks at ambient temperatures ranging from 18° C. to 24° C.

*Root description*.—Medium in thickness, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Outwardly spreading, mounding to trailing plant habit with about four primary lateral branches each with about three to four secondary lateral branches developing per plant; dense and bushy appearance; pinching enhances development of lateral branches; moderately vigorous growth habit.

*Plant height, soil level to top of foliar plane*.—About 17.5 cm.

*Plant height, soil level to top of floral plane*.—About 19.5 cm.

*Plant diameter* (*area of spread*).—About 25 cm by 30 cm.

*Lateral branches*.—Length: About 19 cm. Diameter: About 2.5 mm. Internode length: About 1 cm to 3.5 cm. Strength: Strong. Aspect: About 45° to 55° from vertical. Texture and luster: Pubescent; matte. Color, developing: Close to 146D. Color, developed: Close to 146B.

Leaf description:

*Arrangement*.—Alternate before flowering; opposite after flowers develop; simple.

*Length*.—About 4.5 cm.

*Width*.—About 2.4 cm.

*Shape*.—Elliptical.

*Apex*.—Acute to rounded.

*Base*.—Attenuate.

*Margin*.—Entire.

*Texture and luster, upper and lower surfaces*.—Pubescent; matte.

*Venation pattern*.—Pinnate, arcuate.

*Color*.—Developing leaves, upper surface: Close to 146A. Developing leaves, lower surface: Close to 146B. Fully expanded leaves, upper surface: Close to 137B; venation, close to 146B. Fully expanded leaves, lower surface: Close to 146B; venation, close to 146C.

*Petioles*.—Length: About 5 mm. Diameter: About 3 mm. Strength: Strong. Texture and luster, upper and lower surfaces: Minute pubescence; slightly glandular; matte. Color, upper and lower surfaces: Close to 146C.

Flower description:

*Flower type and flowering habit*.—Single axillary salverform flowers; flowers face mostly upright to somewhat outwardly; freely flowering habit with about 54 flowers potentially developing per plant.

*Natural flowering season*.—Long day responsive; long flowering period, plants flower from early spring until frost in the autumn, flowering continuous during this period; early flowering habit, plants begin flowering about six weeks after planting.

*Flower longevity on the plant*.—About four to five days; flowers persistent.

*Fragrance*.—Faint, sweet.

*Flower buds*.—Length: About 4.6 cm. Diameter: About 6 mm. Shape: Elongate. Texture and luster: Pubescent; matte. Color: Close to 91C.

*Flower diameter*.—About 5.2 cm.

*Flower depth* (*height*).—About 5.5 cm.

*Throat diameter, distal*.—About 1.2 cm.

*Tube length*.—About 3.5 cm.

*Tube diameter, proximal*.—About 3 mm.

*Petals*.—Quantity and arrangement: Five petals fused in a single salverform whorl. Petal lobe length (from throat): About 2.3 cm. Petal lobe width: About 2.5 cm. Petal lobe shape: Fan-shaped. Petal lobe apex: Bluntly acute. Petal lobe margin: Entire; slightly to moderately undulate. Petal lobe texture and luster, upper surface: Smooth, glabrous; velvety; matte. Petal lobe texture and luster, lower surface: Minute pubescence; matte. Throat texture and luster: Smooth, glabrous; matte. Tube texture and luster: Pubescent; matte. Color: When opening, upper surface: Close to N88B. When opening, lower surface: Close to N88D. Fully opened, upper surface: Close to N88B; venation, close to 83D; color becoming closer to 90D with development. Fully opened, lower surface: Close to N88C to N88D; venation, close to 144B; color becoming closer to 91B with development. Flower throat (inside): Close to 154C to 154D; venation, close to 145B. Flower tube (outside): Close to 145C to 145D; venation, close to 145A.

*Sepals*.—Quantity and arrangement: Five sepals fused in a single star-shaped whorl. Length: About 2 cm. Width: About 4 mm. Shape: Lanceolate. Apex:

Broadly acute. Margin: Entire. Texture and luster, upper and lower surfaces: Pubescent; matte. Color, when developing, upper and lower surfaces: Close to N137A. Color, fully developed, upper and lower surfaces: Close to 146A.

*Peduncles*.—Length: About 2.5 cm. Width: About 5 mm. Angle: About 45° to 65° from the stem axis. Strength: Strong. Texture and luster: Pubescent; matte. Color: Close to 146C.

*Reproductive organs*.—Stamens: Quantity per flower: Five. Filament length: About 2.2 cm. Filament color: Close to 145D. Anther size: About 1 mm by 2 mm. Anther shape: Oval. Anther color: Close to 160D. Pollen amount: None observed. Pistils: Quantity per flower: One. Pistil length: About 2.5 cm. Style length: About 2.1 cm. Style color: Close to 145C. Stigma diameter: About 1.5 mm. Stigma shape: Round. Stigma color: Close to 145B. Ovary color: Close to 145A.

*Seeds and fruits*.—To date, seed and fruit development has not been observed on plants of the new *Petunia*.

Pathogen & pest resistance: To date, plants of the new *Petunia* have not been noted to be resistant to pathogens or pests common to *Petunia* plants.

Garden performance: Plants of the new *Petunia* have been observed to have good garden performance and have been observed to tolerate rain, wind and temperatures ranging from about 2° C. to about 40° C. and to be suitable for USDA Hardiness Zones 10a to 11b.

It is claimed:

1. A new and distinct *Petunia* plant named 'KL1117mut1' as illustrated and described.

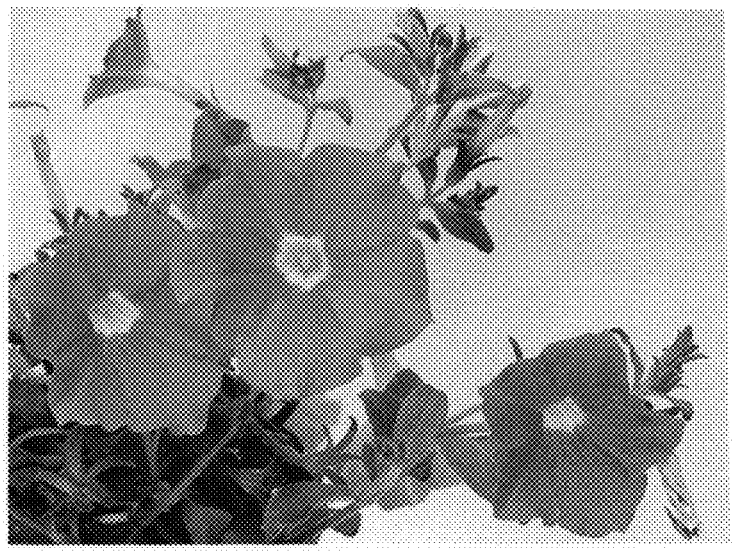
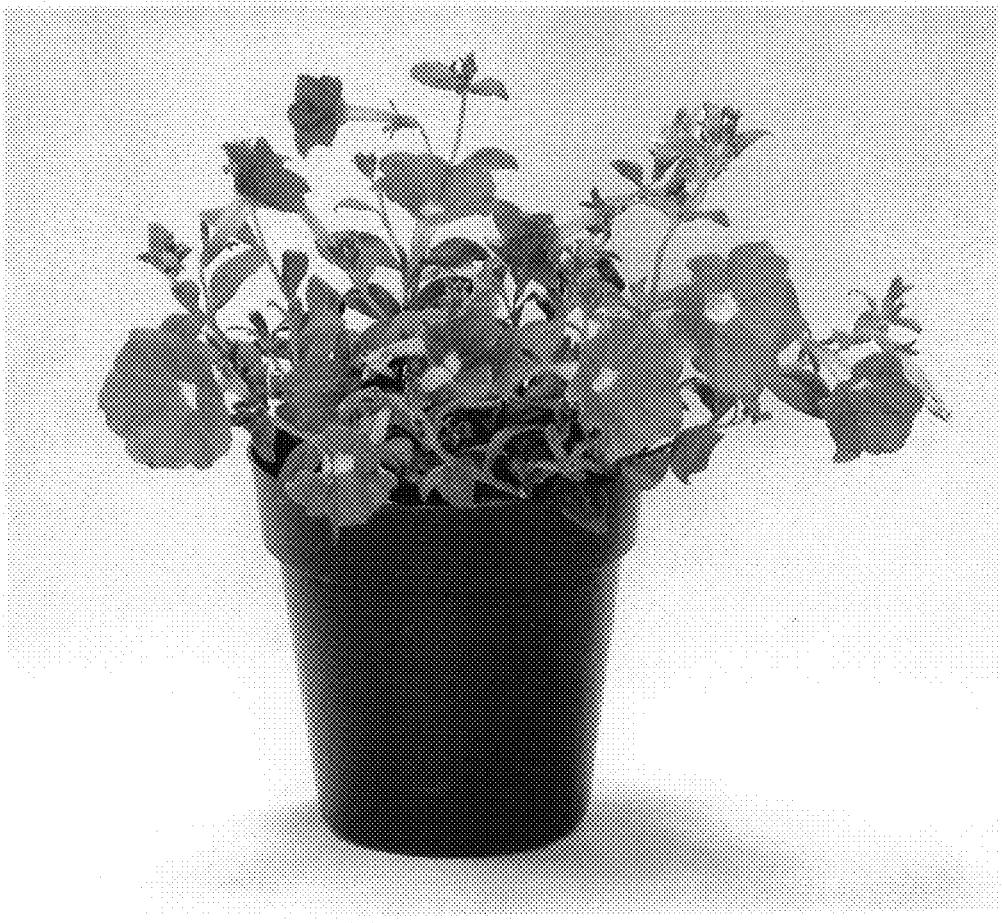

* * * * *